United States Patent
Ge et al.

(10) Patent No.: US 11,066,403 B2
(45) Date of Patent: Jul. 20, 2021

(54) SOLID FORM OF AZETIDINE DERIVATIVE AND PREPARATION METHOD THEREFOR AND USE THEREOF

(71) Applicant: SICHUAN KELUN-BIOTECH BIOPHARMACEUTICAL CO., LTD., Sichuan (CN)

(72) Inventors: Jianhua Ge, Chengdu (CN); Zengying Han, Chengdu (CN); Fengchun Chen, Chengdu (CN); Shihu Jiao, Chengdu (CN); Hong Zhang, Chengdu (CN); Ping Zhang, Chengdu (CN); Lichun Wang, Chengdu (CN); Jingyi Wang, Chengdu (CN)

(73) Assignee: SICHUAN KELUN-BIOTECH BIOPHARMACEUTICAL CO., LTD., Sichuan (CN)

( * ) Notice: Subject to any disclaimer, the term of this patent is extended or adjusted under 35 U.S.C. 154(b) by 0 days.

(21) Appl. No.: 16/499,610

(22) PCT Filed: May 28, 2018

(86) PCT No.: PCT/CN2018/088645
§ 371 (c)(1),
(2) Date: Sep. 30, 2019

(87) PCT Pub. No.: WO2018/223859
PCT Pub. Date: Dec. 13, 2018

(65) Prior Publication Data
US 2020/0039978 A1 Feb. 6, 2020

(30) Foreign Application Priority Data
Jun. 7, 2017 (CN) .......................... 201710421771.1

(51) Int. Cl.
C07D 471/04 (2006.01)
A61P 19/02 (2006.01)
(52) U.S. Cl.
CPC ............ C07D 471/04 (2013.01); A61P 19/02 (2018.01); C07B 2200/13 (2013.01)
(58) Field of Classification Search
CPC .......................... C07D 471/04; C07B 2200/13
See application file for complete search history.

(56) References Cited

U.S. PATENT DOCUMENTS

| | | |
|---|---|---|
| 2018/0044342 A1 | 2/2018 | Chen et al. |
| 2018/0289680 A1 | 10/2018 | Xie et al. |

FOREIGN PATENT DOCUMENTS

| | | |
|---|---|---|
| WO | WO 2007/056596 A2 | 5/2007 |
| WO | WO 2009/114512 A1 | 9/2009 |
| WO | WO 2010/039939 A1 | 4/2010 |
| WO | WO 2013/173506 A2 | 11/2013 |
| WO | WO 2015/166434 A1 | 11/2015 |
| WO | WO 2016/026975 A1 | 2/2016 |
| WO | WO 2016/074650 A1 | 5/2016 |
| WO | WO 2017/008772 A1 | 1/2017 |
| WO | WO 2017/082759 A1 | 5/2017 |
| WO | WO 2017/125097 A1 | 7/2017 |
| WO | WO 2017/125772 A1 | 7/2017 |

OTHER PUBLICATIONS

Roskoski. Pharmacological Research, 2016, 111, 784-803. (Year: 2016).*
"Type 1 diabetes—prevention", http://diabetes.webmd.com/tc/type-1-diabetes-prevention, accessed May 26, 2009 (Year: 2009).*
ISA—State Intellecual Property Office of the P.R. China; International Search Report of PCT/CN2018/088645; dated Jul. 19, 2018.
International Searching Authority for PCT/CN/2018/088645; Written Opinion dated Aug. 1, 2018.
European Patent Office; Supplementary European Search Report; EP Application No. 18 81 4274.9; dated Feb. 5, 2021.

* cited by examiner

*Primary Examiner* — Noble E Jarrell
(74) *Attorney, Agent, or Firm* — Kilpatrick Townsend & Stockton LLP

(57) ABSTRACT

The present invention relates to a solid form of a compound of Formula (I), a method for preparing the solid form, a pharmaceutical composition comprising the solid form, and use of the solid form in the treatment of Janus kinase (JAK) related diseases comprising, for example, inflammatory diseases, autoimmune diseases, and cancers.

Formula (I)

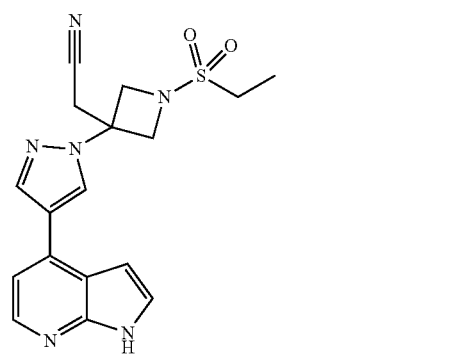

49 Claims, 3 Drawing Sheets

SOLID FORM OF AZETIDINE DERIVATIVE AND PREPARATION METHOD THEREFOR AND USE THEREOF

CROSS-REFERENCE TO RELATED APPLICATIONS

This application is a National Phase Entry of PCT/CN2018/088645, filed May 28, 2018, which claims the benefit of priority to CN Patent Application No. 201710421771.1, filed Jun. 7, 2017, the teachings of which are hereby incorporated by reference in their entireties for all purposes.

FIELD OF THE INVENTION

The present invention relates to a solid form of 2-(3-(4-(1H-pyrrolo[2,3-b]pyridin-4-yl)-1H-pyrazol-1-yl)-1-(ethyl-sulfonyl)azetidin-3-yl)acetonitrile (hereinafter referred to as "the compound of Formula (I)"), a preparation method therefor, a pharmaceutical composition comprising the same, and the use thereof for the treatment of Janus kinase (JAK) related diseases comprising, for example, inflammatory diseases, autoimmune diseases, and cancers.

BACKGROUND OF THE INVENTION

Rheumatoid arthritis is a chronic systemic autoimmune disease characterized by joint lesions. Its main clinical manifestations are joint swelling and pain at the synovium of small joints, followed by cartilage destruction and joint space narrowing, and late joint stiffness, deformity and dysfunction, etc. due to severe bone destruction and resorption. In China, the prevalence rate of rheumatoid arthritis is 0.24-0.5%, arising more frequently in females than males (about 2-3:1), and it occurs at all ages (most between 20-50 years old). Nowadays, there is no good radical cure of the disease which is associated with high rates of recurrence, disability and a poor prognosis.

Nonsteroidal anti-inflammatory drugs (NSAIDs) are preferred drugs for the treatment of this disease. It works mainly by inhibiting the activity of cyclooxygenase and reducing the synthesis of prostaglandin. Thereby it could relieve pain and swelling of the joint, and improve joint functions in patients suffering from rheumatoid arthritis. But it cannot stop the progression of the disease, and may cause a variety of significant toxic and side effects after long-term administration. Biological products can also be used for treatment, but the costs in the production thereof and in the treatment are unaffordable to the public.

Janus kinase (JAK) is a non-receptor type tyrosine protein kinase, and belongs to the family of protein kinases. The Janus kinase family plays a role in the immune response cell proliferation factor-dependent regulation. The compound of the Formula (I) below is an inhibitor of JAK1/2 and has significant advantages in terms of activity and toxicity:

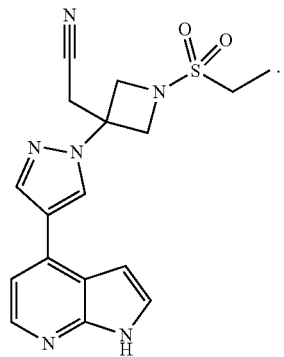

Formula (I)

SUMMARY OF THE INVENTION

An aspect of the present invention provides crystalline forms of the following compound of Formula (I):

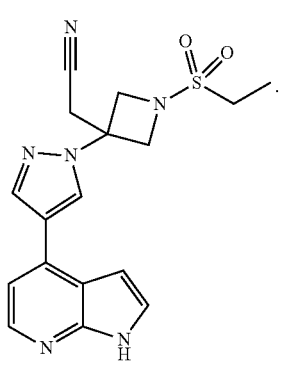

Formula (I)

Another aspect of the present invention provides a method for the preparation of the crystalline forms of the present invention.

Another aspect of the present invention provides a pharmaceutical composition comprising any one or more of the crystalline forms of the present invention and one or more pharmaceutically acceptable carriers.

Another aspect of the present invention provides use of the crystalline forms or pharmaceutical compositions of the present invention in the manufacture of a medicament for the prophylaxis or treatment of a JAK-related disease.

Another aspect of the present invention provides the crystalline forms or pharmaceutical compositions of the present invention for the prophylaxis or treatment of a JAK-related disease.

Another aspect of the present invention provides a method for the prophylaxis or treatment of a JAK-related disease, comprising administering to a subject in need thereof an effective amount of one or more crystalline forms or pharmaceutical compositions of the present invention.

The preferred crystalline forms of the present invention not only have excellent effects and lower toxic and side effects in preventing or treating a JAK-related disease, but also have other advantages. For example, the preferred crystalline forms of the compound of Formula (I) of the present invention have excellent physical properties (including solubility, dissolution rate, light stability, low hygroscopicity, high temperature resistance, high humidity resistance, fluidity, thermal stability, and the like), and the preferred crystalline forms of the present invention may have superior properties in terms of bioavailability, physical and/or chemical stability, lipid solubility, and ease of preparation. The preferred crystalline forms of the present invention are more suitable and convenient for large scale production and for preparing a formulation, can reduce irritation and enhance absorption, solve problems in metabolic rates, significantly decrease toxicity, improve safety, and effectively ensure the quality and efficacy of the pharmaceutical products.

DETAILED DESCRIPTION OF THE INVENTION

Figure 1:
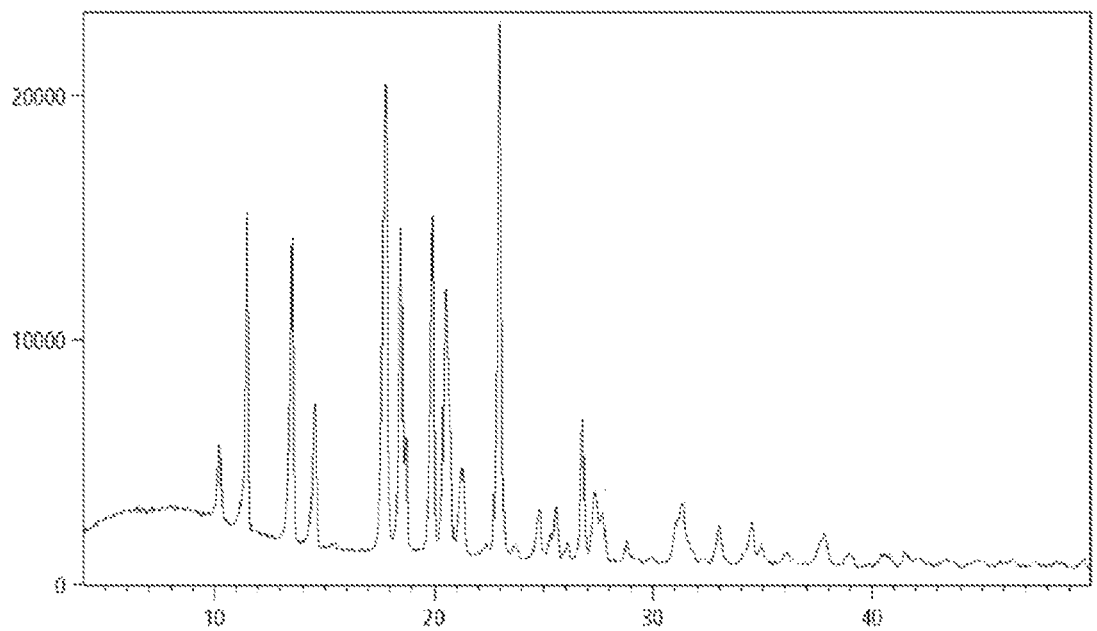
FIG. 1 shows an X-ray powder diffraction (XRPD) spectrum of crystalline form A of the compound of Formula (I).

Unless otherwise defined in the context, all technical and scientific terms used herein are intended to have the same meaning as commonly understood by a person skilled in the art. References to techniques employed herein are intended to refer to the techniques as commonly understood in the art, including those variations on techniques or substitutions of equivalent techniques which would be apparent to a person skilled in the art. While it is believed that the following terms will be readily understood by a person skilled in the art, the following definitions are nevertheless put forth to better illustrate the present invention.

The terms "contain", "include", "comprise", "have", or "relate to", as well as other variations used herein are inclusive or open-ended, and do not exclude additional, unrecited elements or method steps.

The word "about" as used herein refers to, as appreciated by a person skilled in the art, a range within the acceptable standard error of a value, such as ±0.05, ±0.1, ±0.2, ±0.3, ±0.5, ±1, ±2 or ±3, etc.

The term "solid form" as used herein includes all solid forms of the compounds of Formula (I), such as a crystalline form or amorphous form.

The term "amorphous" as used herein refers to any solid substance which lacks order in three dimensions. In some instances, amorphous solids can be characterized by known techniques, including XRPD crystal diffraction analysis, solid state nuclear magnet resonance (ssNMR) spectral analysis, differential scanning calorimetry (DSC), or some combination of these techniques. As illustrated below, amorphous solids give XRPD spectrums with no clear diffraction characteristic peaks.

The term "crystalline form" or "crystal" as used herein refers to any solid substance exhibiting three-dimensional order, which in contrast to an amorphous solid substance, gives a distinctive XRPD spectrum with sharp and defined peaks.

The term "X-ray powder diffraction spectrum (XRPD spectrum)" as used herein refers to the experimentally observed diffractogram or parameters, data or values derived therefrom. XRPD spectrums are usually characterized by peak positions (abscissa) and peak intensities (ordinate).

The term "2θ" as used herein refers to the peak position in degrees (°) based on the setup of the X-ray diffraction experiment and is generally the unit on abscissa in diffraction patterns. The experimental setup requires that if a reflection is diffracted when the incoming beam forms an angle theta (θ) with a certain lattice plane, the reflected beam is recorded at an angle 2 theta (2θ). It should be understood that reference herein to specific 2θ values for a specific crystalline form is intended to mean the 2θ values (in degrees) as measured using the X-ray diffraction experimental conditions as described herein. For example, as described herein, Cu-Kα (Kα1 (Å): 1.540598 and Kα2 (Å): 1.544426 Å) was used as the source of radiation.

The term "differential scanning calorimetry (DSC) graph" as used herein refers to a curve recorded on a differential scanning calorimeter.

The term "thermogravimetric analysis (TGA) graph" as used herein refers to a curve recorded on a thermogravimetric analyzer.

As used herein, the term "essentially the same" means that typical peak position and/or intensity variability are taken into account. For example, for X-ray diffraction peaks, one skilled in the art will appreciate that the peak positions (2θ) will show some variability, typically as much as 0.1 to 0.2 degree, and the apparatus for measuring the diffraction may also lead to some variability. Further, one skilled in the art will appreciate that relative peak intensities will vary due to difference between apparatuses as well as degree of crystallinity, preferred orientation, prepared sample surface, and other factors known to those skilled in the art, and should be taken as qualitative measures only.

The term "alcohol" as used herein preferably means alcohols having 1 to 10 carbon atoms, including, but not limited to, methanol, ethanol, 1-propanol, 2-propanol (isopropanol), 1-butanol, 2-butanol and tert-butanol.

The term "nitrile" as used herein preferably means nitriles having 2 to 6 carbon atoms, including, but not limited to, acetonitrile and propionitrile.

The term "amide" as used herein preferably means amides having 1 to 10 carbon atoms, including, but not limited to, N,N-dimethylformamide or N,N-dimethylacetamide.

The term "ketone" as used herein preferably means ketones having 3 to 6 carbon atoms, including, but not limited to, acetone, butanone, methyl ethyl ketone, methyl isobutyl ketone, and diethyl ketone.

The term "ether" as used herein preferably means ethers having 2 to 10 carbon atoms, including chain ethers and cyclic ethers (e.g., furans (including tetrahydrofurans) and dioxanes), specifically including, but not limited to, diethyl ether, diisopropyl ether, methyl tert-butyl ether, tetrahydrofuran, 2-methyltetrahydrofuran, dioxane, cyclopentyl methyl ether, anisole and dimethoxyethane.

The term "ester" as used herein preferably means esters having 3 to 10 carbon atoms, including, but not limited to, ethyl acetate, propyl acetate, isopropyl acetate, ethyl isopropionate, dimethyl carbonate and butyl acetate.

The term "halogenated alkane" as used herein preferably means halogenated alkanes having 1 to 10 carbon atoms, including, but not limited to, dichloromethane, trichloromethane (chloroform).

The prepared solid form (preferably crystalline form) can be isolated and recovered by methods including decantation, centrifugation, evaporation, gravity filtration, suction filtration, or any other technique for the isolation of solids under pressure or under reduced pressure. The isolated solid can optionally be dried. "Drying" in the present invention can be carried out under blast or reduced pressure (preferably in vacuum), at any temperature (preferably room temperature), until the residual solvent amount is reduced to the level within the acceptable ranges given in the International Conference on Harmonisation of Technical Requirements for Registration of Pharmaceuticals for Human Use ("ICH") guidelines. The residual solvent amount depends on the type of the solvent, but does not exceed about 5000 ppm, or preferably about 4000 ppm, or more preferably about 3000 ppm. Drying can be carried out in a tray dryer, vacuum oven, air oven, cone vacuum dryer, rotary vacuum dryer, fluidized bed dryer, spin flash dryer, flash dryer, or the like. The drying can be carried out at a temperature lower than about 100° C., lower than about 80° C., lower than about 60° C., lower than about 50° C., lower than about 30° C., or any other suitable temperature, at atmospheric pressure or under a reduced pressure (preferably in vacuum) for any desired period (e.g., about 1, 2, 3, 5, 10, 15, 20, 24 hours or overnight) until the desired result is achieved. The drying can be carried out any desired times until the desired product quality is achieved. The dried product can optionally be subjected to a size reduction procedure to produce desired particle sizes Milling or micronization can be performed before drying, or after the completion of drying of the product. Techniques that can be used for particle size reduction include, but are not limited to, ball milling, roller milling and hammer milling, as well as jet milling Crystalline Form and Preparation Method Therefor In some embodiments, the present invention provides crystalline form A of the compound of Formula (I), and the XRPD spectrum of the crystalline form A comprises peaks at diffraction angles (2θ) of about 10.2±0.2, 11.5±0.2, 13.5±0.2, 14.6±0.2, 17.8±0.2, 18.5±0.2 and 19.9±0.2 degrees (°). Preferably, the XRPD spectrum of the crystalline form A comprises peaks at diffraction angles (2θ) of about 10.2±0.2, 11.5±0.2, 13.5±0.2, 14.6±0.2, 17.8±0.2, 18.5±0.2, 18.7±0.2, 19.9±0.2, 20.5±0.2, 23.0±0.2 and 26.8±0.2 degrees.

More preferably, the XRPD spectrum of the crystalline form A comprises peaks characterized by the following parameters:

| 2θ (°) | Interplanar spacing d (Å) | Relative intensity I/I₀ (%) |
|---|---|---|
| 10.2 ± 0.2 | 8.7 ± 0.5 | 15.9 ± 0.5 |
| 11.5 ± 0.2 | 7.7 ± 0.5 | 71.5 ± 0.5 |
| 13.5 ± 0.2 | 6.6 ± 0.5 | 50.2 ± 0.5 |
| 14.6 ± 0.2 | 6.1 ± 0.5 | 27.1 ± 0.5 |
| 17.8 ± 0.2 | 5.0 ± 0.5 | 92.3 ± 0.5 |
| 18.5 ± 0.2 | 4.8 ± 0.5 | 100.0 ± 0.5 |
| 18.7 ± 0.2 | 4.8 ± 0.5 | 18.4 ± 0.5 |
| 19.9 ± 0.2 | 4.5 ± 0.5 | 78.6 ± 0.5 |
| 20.5 ± 0.2 | 4.3 ± 0.5 | 52.6 ± 0.5 |
| 21.0 ± 0.2 | 4.2 ± 0.5 | 12.2 ± 0.5 |
| 21.2 ± 0.2 | 4.2 ± 0.5 | 14.9 ± 0.5 |
| 22.3 ± 0.2 | 4.0 ± 0.5 | 1.7 ± 0.5 |
| 23.0 ± 0.2 | 3.9 ± 0.5 | 92.3 ± 0.5 |
| 23.6 ± 0.2 | 3.8 ± 0.5 | 1.2 ± 0.5 |
| 24.7 ± 0.2 | 3.6 ± 0.5 | 5.1 ± 0.5 |
| 25.2 ± 0.2 | 3.5 ± 0.5 | 2.1 ± 0.5 |
| 25.5 ± 0.2 | 3.5 ± 0.5 | 8.2 ± 0.5 |
| 26.1 ± 0.2 | 3.4 ± 0.5 | 1.9 ± 0.5 |
| 26.8 ± 0.2 | 3.3 ± 0.5 | 22.2 ± 0.5 |
| 27.3 ± 0.2 | 3.3 ± 0.5 | 10.4 ± 0.5 |
| 27.7 ± 0.2 | 3.2 ± 0.5 | 9.2 ± 0.5 |

In preferred embodiments, the XRPD spectrum of the crystalline form A of the compound of Formula (I) comprises peaks at diffraction angles (2θ) essentially the same as shown in FIG. 1. In the most preferred embodiments, the XRPD spectrum of the crystalline form A of the compound of Formula (I) shows the peak positions essentially the same as shown in FIG. 1.

In preferred embodiments, the DSC graph of the crystalline form A of the compound of Formula (I) of the present invention comprises a characteristic peak at about (190.6±0.5)-(194.5±0.5)° C.

Figure 2:
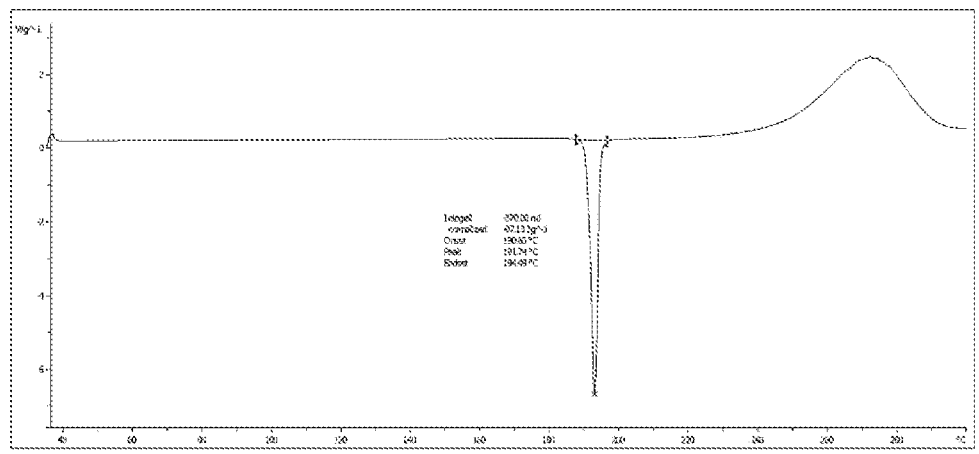
FIG. 2 shows a differential scanning calorimetry (DSC) graph of crystalline form A of the compound of Formula (I).

In more preferred embodiments, the DSC graph of the crystalline form A of the compound of Formula (I) comprises a characteristic peak at a temperature essentially the same as shown in FIG. 2. In the most preferred embodiments, the characteristic peak position in the DSC graph of crystalline form A of the compound of Formula (I) is essentially the same as shown in FIG. 2.

In preferred embodiments, the TGA graph of the crystalline form A of the compound of Formula (I) of the present invention comprises two characteristic peaks at about 272.7±0.5° C. and 347.2±0.5° C., respectively.

Figure 3:
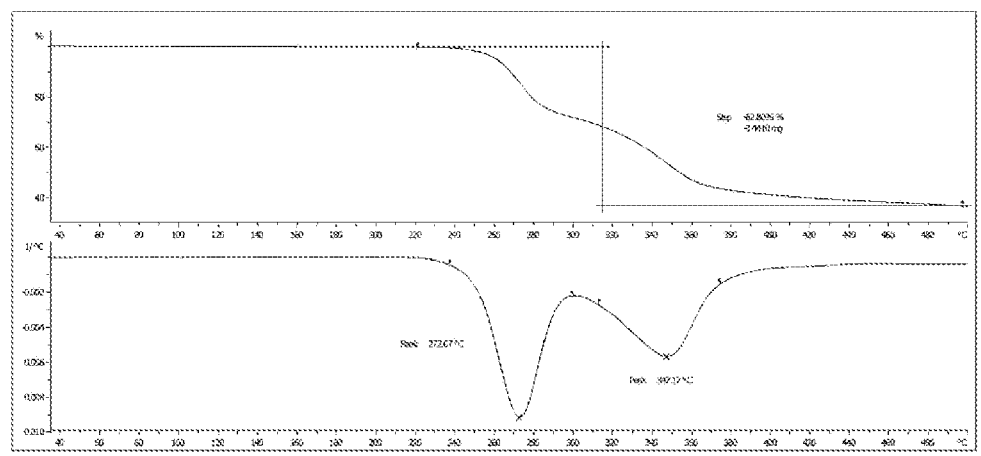
FIG. 3 shows a thermogravimetric analysis (TGA) graph of crystalline form A of the compound of Formula (I).

In more preferred embodiments, the TGA graph of the crystalline form A of the compound of Formula (I) comprises characteristic peaks at a temperature essentially the same as shown in FIG. 3. In the most preferred embodiments, the characteristic peak positions in the TGA graph of crystalline form A of the compound of Formula (I) are essentially the same as shown in FIG. 3.

In some embodiments, the present invention provides a method for the preparation of crystalline form A as mentioned above, and the method includes, but is not limited to, a natural cooling method and an anti-solvent addition method.

In some embodiments, the present invention provides a method for the preparation of crystalline form A as mentioned above, and the method is a natural cooling method, which comprises adding the compound of Formula (I) to a solvent, heating and stirring to dissolve it, then removing heating, and allowing the resulting solution to be cooled under stirring, and filtering the solid precipitated from the solution to afford the crystalline form A.

In preferred embodiments, the solvent includes, but is not limited to, an organic solvent, such as an alcohol solvent, a nitrile solvent, a ketone solvent, an ether solvent, a halogenated alkane solvent, an amide solvent, or an ester solvent, and in particular, e.g., acetonitrile, propionitrile, ethanol, methanol, 1-propanol (n-propanol), 1-butanol, diethyl ether, tetrahydrofuran, dioxane, acetone, butanone, dichloromethane, trichloromethane (chloroform), N,N-dimethylformamide, N,N-dimethylacetamide, ethyl acetate, or a mixed solvent of two or more of the above solvents. In some embodiments, the solvent is a mixed solvent of an alcohol solvent and a nitrile solvent. In some embodiments, the solvent is a mixed solvent of ethanol and acetonitrile.

In preferred embodiments, the weight/volume ratio (g/mL) of the compound of Formula (I) to the solvent is 1:1 to 1:80, preferably 1:5 to 1:30. In some embodiments, the weight/volume ratio (g/mL) of the compound of Formula (I) to the solvent is 1:10, 1:15, 1:20, 1:25, 1:40, 1:50, 1:60, or 1:70.

In preferred embodiments, when the solvent is a mixed solvent of two solvents, the volume ratio between the two solvents is (1-30):(30-1). In some embodiments, the volume ratio between the two solvents is 1:5, 1:10, 1:15, 1:20, 1:25, 1:30, 30:1, 25:1, 20:1, 15:1, 10:1, 5:1, or 1:1.

In preferred embodiments, the temperature at the end of the cooling is 10-30° C., e.g., 20-25° C.

In some embodiments, the present invention provides a method for the preparation of crystalline form A as mentioned above, and it is an anti-solvent addition method, which comprises dissolving the compound of Formula (I) in a good solvent, then adding an antisolvent to the resultant solution, and stirring to precipitate the solid, and filtering the precipitates to afford the crystalline form A.

In preferred embodiments, the good solvent includes, but is not limited to, an organic solvent, such as an alcohol solvent, a nitrile solvent, a ketone solvent, an ether solvent, a halogenated alkane solvent, an amide solvent, or an ester solvent, and in particular, e.g., acetonitrile, propionitrile, ethanol, methanol, 1-propanol (n-propanol), 1-butanol, diethyl ether, tetrahydrofuran, dioxane, acetone, butanone, dichloromethane, trichloromethane (chloroform), dimethylformamide, dimethylacetamide, or ethyl acetate. In some embodiments, the antisolvent includes, but is not limited to, an inorganic solvent, e.g., water.

In preferred embodiments, the volume ratio of the good solvent to the antisolvent is (0.2-1):(1-20), preferably 1:(1-10). In some embodiments, the weight/volume ratio (g/mL) of the compound of Formula (I) to the good solvent is 1:(1-20), preferably 1:(1-10).

In some embodiments, the present invention provides crystalline form B of the compound of Formula (I), and the XRPD spectrum of the crystalline form B comprises peaks at diffraction angles (2θ) of about 6.4±0.2, 7.9±0.2, 8.4±0.2, 11.8±0.2, 12.7±0.2, 16.0±0.2, 16.3±0.2 and 19.1±0.2 degrees. Preferably, the XRPD spectrum of the crystalline form B comprises peaks at diffraction angles (2θ) of about 6.4±0.2, 7.9±0.2, 8.4±0.2, 11.8±0.2, 12.7±0.2, 15.5±0.2, 16.0±0.2, 16.3±0.2, 16.9±0.2, 19.1±0.2 and 23.5±0.2 degrees.

More preferably, the XRPD spectrum of the crystalline form B comprises peaks characterized by the following parameters:

| 2θ (°) | Interplanar spacing d (Å) | Relative intensity I/I₀ (%) |
|---|---|---|
| 6.4 ± 0.2 | 13.7 ± 0.5 | 8.0 ± 0.5 |
| 7.9 ± 0.2 | 11.1 ± 0.5 | 66.7 ± 0.5 |
| 8.4 ± 0.2 | 10.5 ± 0.5 | 39.6 ± 0.5 |
| 11.8 ± 0.2 | 7.5 ± 0.5 | 10.0 ± 0.5 |
| 12.7 ± 0.2 | 7.0 ± 0.5 | 11.0 ± 0.5 |
| 15.5 ± 0.2 | 5.7 ± 0.5 | 13.1 ± 0.5 |
| 16.0 ± 0.2 | 5.5 ± 0.5 | 44.2 ± 0.5 |
| 16.3 ± 0.2 | 5.4 ± 0.5 | 31.8 ± 0.5 |
| 16.9 ± 0.2 | 5.2 ± 0.5 | 13.2 ± 0.5 |
| 17.4 ± 0.2 | 5.1 ± 0.5 | 5.2 ± 0.5 |
| 18.4 ± 0.2 | 4.8 ± 0.5 | 3.8 ± 0.5 |
| 19.1 ± 0.2 | 4.6 ± 0.5 | 48.8 ± 0.5 |
| 19.5 ± 0.2 | 4.5 ± 0.5 | 15.7 ± 0.5 |
| 20.7 ± 0.2 | 4.3 ± 0.5 | 3.2 ± 0.5 |
| 21.3 ± 0.2 | 4.2 ± 0.5 | 8.0 ± 0.5 |
| 21.9 ± 0.2 | 4.1 ± 0.5 | 10.0 ± 0.5 |
| 22.4 ± 0.2 | 4.0 ± 0.5 | 16.9 ± 0.5 |
| 23.2 ± 0.2 | 3.8 ± 0.5 | 31.6 ± 0.5 |
| 23.5 ± 0.2 | 3.8 ± 0.5 | 100.0 ± 0.5 |
| 24.5 ± 0.2 | 3.6 ± 0.5 | 6.4 ± 0.5 |
| 26.0 ± 0.2 | 3.4 ± 0.5 | 2.2 ± 0.5 |
| 28.0 ± 0.2 | 3.2 ± 0.5 | 10.9 ± 0.5 |

Figure 4:
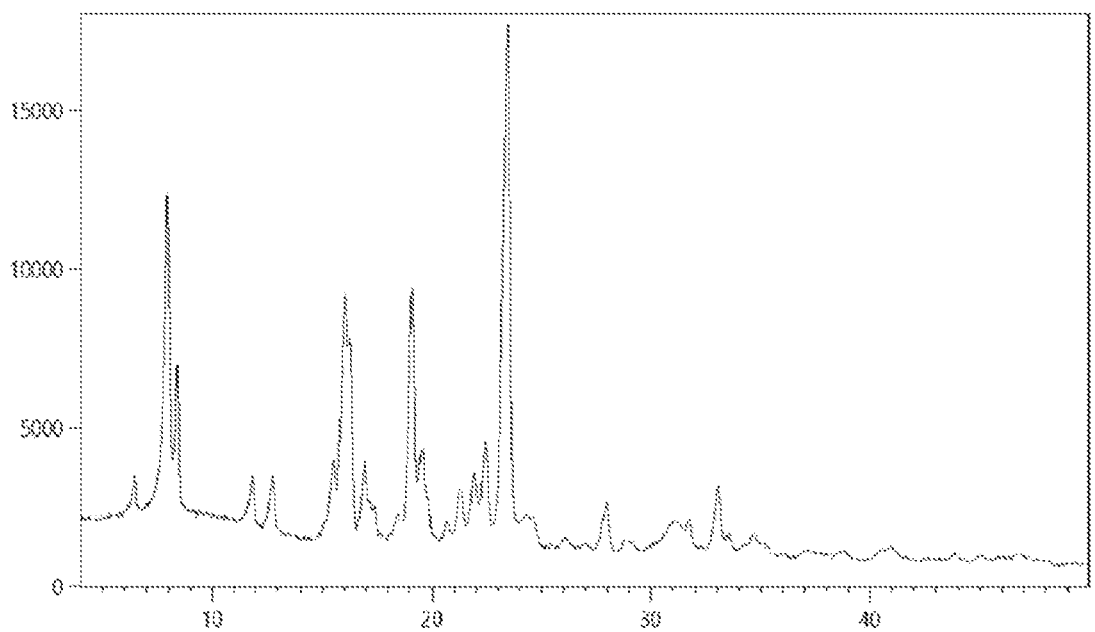
FIG. 4 shows an XRPD spectrum of crystalline form B of the compound of Formula (I).

In preferred embodiments, the XRPD spectrum of the crystalline form B of the compound of Formula (I) comprises peaks at diffraction angles (2θ) essentially the same as shown in FIG. 4. In the most preferred embodiments, the XRPD spectrum of the crystalline form B of the compound of Formula (I) shows peak positions essentially the same as shown in FIG. 4.

In preferred embodiments, the DSC graph of the crystalline form B of the compound of Formula (I) of the present invention comprises characteristic peaks at about (77.5±0.5)-(84.7±0.5)° C., (87.0±0.5)–(97.3±0.5)° C. and (192.1±0.5)-(195.3±0.5)° C.

Figure 5:
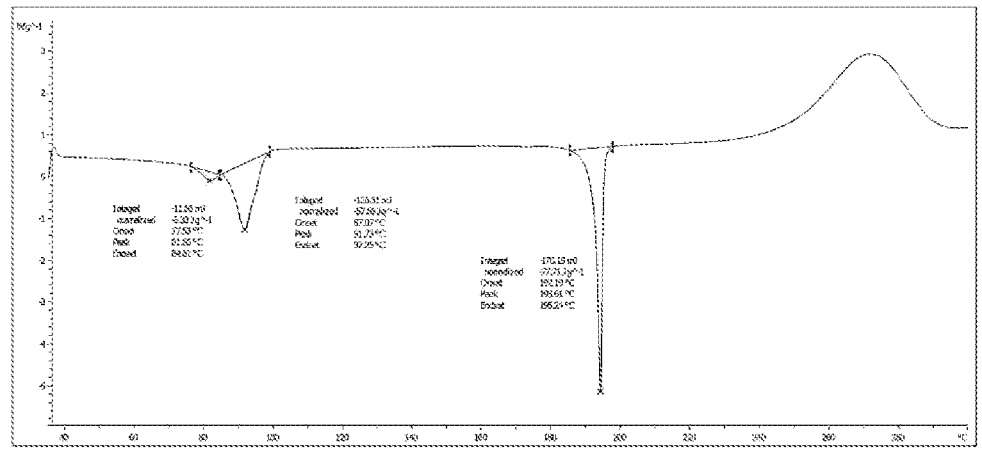
FIG. 5 shows a DSC graph of crystalline form B of the compound of Formula (I).

In a more preferred embodiment, the DSC graph of the crystalline form B of the compound of Formula (I) comprises characteristic peaks at a temperature essentially the same as shown in FIG. 5. In the most preferred embodiment, the characteristic peak positions in the DSC graph of crystalline form B of the compound of Formula (I) are essentially the same as shown in FIG. 5.

In preferred embodiments, the TGA graph of the crystalline form B of the compound of Formula (I) of the present invention comprises three characteristic peaks at about 82.0±0.5° C., 271.0±0.5° C. and 331.0±0.5° C., respectively.

Figure 6:
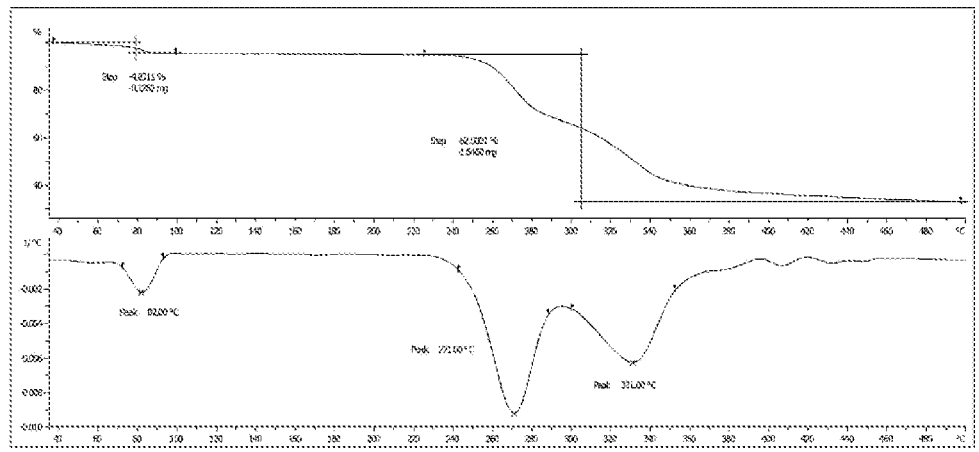
FIG. 6 shows a TGA graph of crystalline form B of the compound of Formula (I).

In more preferred embodiments, the TGA graph of the crystalline form B of the compound of Formula (I) comprises characteristic peaks at a temperature essentially the same as shown in FIG. 6. In the most preferred embodiment, the characteristic peak positions in the TGA graph of crystalline form B of the compound of Formula (I) are essentially the same as shown in FIG. 6.

In some embodiments, the present invention provides a method for the preparation of crystalline form B as mentioned above, which comprises reacting the compound of Formula (I) with an acid in an organic solvent, filtering the precipitated salt, adding it to an inorganic solvent to react with a base, and filtering the precipitated solid to afford the crystalline form B.

In preferred embodiments, the organic solvent includes, but is not limited to, an alcohol solvent, a nitrile solvent, a ketone solvent, an ether solvent, a halogenated alkane solvent, an amide solvent, or an ester solvent, and in particular, e.g., acetonitrile, propionitrile, ethanol, methanol, 1-propanol (n-propanol), 1-butanol, diethyl ether, tetrahydrofuran, dioxane, acetone, butanone, dichloromethane, trichloromethane (chloroform), dimethylformamide, dimethylacetamide, or ethyl acetate. In preferred embodiments, the weight/volume ratio (g/mL) of the compound of Formula (I) to the organic solvent is 1:(1-60), preferably 1:(5-30). In some embodiments, the weight/volume ratio (g/mL) of the compound of Formula (I) to the organic solvent is 1:10, 1:15, 1:20, 1:25, 1:30, 1:40, 1:50, or 1:60.

In preferred embodiments, the compound of Formula (I) as mentioned above is added to the organic solvent, followed by heating so as to dissolve the compound of Formula (I).

In preferred embodiments, the inorganic solvent is preferably water.

The acid includes, but is not limited to, an organic acid such as acetic acid, oxalic acid, citric acid, tartaric acid, methanesulfonic acid, ethanesulfonic acid, or p-toluenesulfonic acid, and an inorganic acid such as hydrochloric acid or sulfuric acid, preferably oxalic acid. In a preferred embodiment, the molar ratio of the compound of Formula (I) to the acid is 1:(1-10), preferably 1:(1-4).

In preferred embodiments, the base includes, but is not limited to, aqueous ammonia, an amine having 1 to 10 carbon atoms (triethylamine, diisopropyl ethylamine), and an hydroxide, an acetate, a carbonate or bicarbonate of an alkali metal (such as sodium, potassium or cesium) or alkaline earth metal (such as magnesium or calcium). In a preferred embodiment, a base is added to adjust the pH of the solution to 7-11, preferably 9-10.

Pharmaceutical Composition and Therapeutic Method

In some embodiments, the present invention provides a pharmaceutical composition comprising any one or more of crystalline forms of the present invention and one or more pharmaceutically acceptable carriers.

In some embodiments, the present invention provides use of crystalline forms of the present invention in the manufacture of a medicament for the prophylaxis or treatment of a JAK-related disease.

In some embodiments, the present invention provides crystalline form A or crystalline form B of the present invention for use in the prophylaxis or treatment of a JAK-related disease.

In some embodiments, the present invention provides a method for the prophylaxis or treatment of a JAK-related disease, comprising administering to a subject in need thereof an effective amount of crystalline forms of the present invention.

The pharmaceutical composition and method of the present invention can be used for the prophylaxis or treatment of JAK-related diseases, such as, but not limited to, immune system diseases (e.g., organ transplant rejection), autoimmune diseases (e.g., multiple sclerosis, rheumatoid arthritis, juvenile arthritis, psoriatic arthritis, type-I diabetes, lupus, psoriasis), allergic conditions (e.g., asthma, food allergy, atopic dermatitis and rhinitis), skin diseases (e.g., psoriasis, atopic dermatitis, rash), solid and hematologic malignancies (e.g., prostate cancer, kidney cancer, liver cancer, pancreatic cancer, gastric cancer, breast cancer, lung cancer, head and neck cancer, thyroid cancer, glioblastoma, leukemia, lymphoma, multiple myeloma), and myeloproliferative disorders (including erythrocytosis, idiopathic thrombocythemia, chronic idiopathic myelofibrosis, myeloid metaplasia with myelofibrosis, chronic myeloid leukemia, chronic myelomonocytic leukemia, chronic eosinophilic leukemia, hypereosinophilic syndrome or systematic mast cell disease). Particularly, the compound of the present invention is for the treatment of JAK-related diseases including e.g., inflammatory diseases, autoimmune diseases, and cancers. More particularly, the compound of the present invention is for the treatment of rheumatoid arthritis.

The term "pharmaceutically acceptable carrier" as used herein refers to a diluent, auxiliary material, excipient, or vehicle with which a therapeutic is administered, and it is, within the scope of sound medical judgment, suitable for use in contact with the tissues of human beings and/or animals without excessive toxicity, irritation, allergic response, or other problem or complication commensurate with a reasonable benefit/risk ratio.

The pharmaceutically acceptable carriers which can be employed in the pharmaceutical composition of the present invention include, but are not limited to, sterile liquids, such as water and oils, including those of petroleum, animal, vegetable or synthetic origin, such as peanut oil, soybean oil, mineral oil, sesame oil and the like. Water is an exemplary carrier when the pharmaceutical composition is administered intravenously. Physiological salines as well as aqueous dextrose and glycerol solutions can also be employed as liquid carriers, particularly for injectable solutions. Suitable pharmaceutical excipients include starch, glucose, lactose, sucrose, gelatin, maltose, chalk, silica gel, sodium stearate, glycerol monostearate, talc, sodium chloride, dried skim milk, glycerol, propylene glycol, water, ethanol and the like. The pharmaceutical composition, if desired, can also contain minor amounts of wetting or emulsifying agents, or pH buffering agents. Oral formulations can include standard carriers such as mannitol, lactose, starch, magnesium stearate, sodium saccharine, cellulose, magnesium carbonate, etc., of pharmaceutical grade. Examples of suitable pharmaceutical carriers are described in e.g., Remington's Pharmaceutical Sciences (1990).

The pharmaceutical composition of the present invention can act systemically and/or topically. To this end, it can be administered through a suitable route, such as through injection, intravenous, intraarterial, subcutaneous, intraperitoneal, intramuscular or transdermal administration, or administered orally, buccally, nasally, transmucosally, topically, as an ophthalmic formulation, or via inhalation.

For these routes of administration, the composition of the present invention can be administered in a suitable dosage form.

Such dosage forms include, but are not limited to tablets, capsules, lozenges, hard candies, powders, sprays, creams, salves, suppositories, gels, pastes, lotions, ointments, aqueous suspensions, injections, elixirs, and syrups.

As used herein, the term "effective amount" refers to the amount of a compound which, after administration, will relieve to some extent one or more of the symptoms of the disorder to be treated.

Dosage regimens can be adjusted to provide the desired optimal response. For example, a single bolus can be administered, several divided doses can be administered over time, or the dose can be proportionally reduced or increased as indicated by the exigencies of the therapeutic situation. It is to be noted that dosage values can vary with the type and severity of the condition to be alleviated, and can include single or multiple doses. It is to be further understood that for any particular subject, specific dosage regimens should be adjusted over time according to the individual need and the professional judgment of the person administering or supervising the administration of the composition.

The amount of the compound of the present invention administered will depend on the subject to be treated, the severity of the disorder or condition, the rate of administration, the disposition of the compound and the discretion of the prescribing physician. Generally, an effective dosage is in the range of about 0.0001 mg to about 50 mg per kg body weight per day, for example about 0.01 mg/kg/day to about 10 mg/kg/day, in single or divided doses. For a 70 kg human, this would amount to about 0.007 mg to about 3500 mg/day, for example about 0.7 mg to about 700 mg/day. In some instances, dosage levels below the lower limit of the aforesaid range may be more than adequate, while in other cases, larger doses can still be employed without causing any harmful side effect, provided that such larger doses are first divided into several small doses for administration throughout the day.

The amount or dosage of the compound of the present invention in the pharmaceutical composition is about 0.01 mg to about 1000 mg, suitably 0.1 mg-500 mg, preferably 0.5 mg-300 mg, more preferably 1 mg-150 mg, particularly preferably 1 mg-50 mg, e.g., 1.5 mg, 2 mg, 4 mg, 10 mg, and 25 mg, etc.

Unless otherwise indicated, the term "treating" or "treatment", as used herein, means reversing, alleviating, inhibiting the progress of, or preventing the disorder or condition to which such term applies, or one or more symptoms of such disorder or condition.

As used herein, the term "subject" includes a human or non-human animal. An exemplary human subject includes a human subject having a disease (such as one described herein) (referred to as a patient), or a normal subject. The term "non-human animal" as used herein includes all vertebrates, such as non-mammals (e.g. birds, amphibians, reptiles) and mammals, such as non-human primates, livestock and/or domesticated animals (such as sheep, dog, cat, cow, pig and the like).

EXAMPLES

The present invention is explained in more detail below with reference to the examples, which are only used to illustrate the technical solutions of the present invention, and are not intended to limit the scope thereof.

Example 1

The compound of Formula (I) (2 g) was added to 20 mL acetonitrile, heated to reflux until the solid completely dissolved. Removing heating, the resulting solution was naturally cooled to 20 to 25° C. under stirring, producing precipitates. The obtained solid was filtered and dried to afford crystalline form A (1.36 g, yield: about 68%).

The obtained crystalline form A was subjected to XRPD analysis, and the resulting XRPD spectrum is shown in FIG. 1, comprising peaks at diffraction angles (2θ) of 10.2±0.2, 11.5±0.2, 13.5±0.2, 14.6±0.2, 17.8±0.2, 18.5±0.2, 18.7±0.2, 19.9±0.2, 20.5±0.2, 23.0±0.2 and 26.8±0.2 degrees.

The obtained crystalline form A was subjected to DSC analysis, and the resulting graph is shown in FIG. 2. According to this analysis, the obtained crystalline form A had an endothermic peak at about (190.6±0.5)-(194.5±0.5)° C.

The obtained crystalline form A was subjected to TGA analysis, and the resulting graph is shown in FIG. 3. According to this analysis, the obtained crystalline form A has two characteristic peaks, and the peak positions are at about 272.7±0.5° C. and 347.2±0.5° C., respectively.

Example 2

The compound of Formula (I) (2 g) was added to 20 mL ethanol and acetonitrile (volume ratio: 1:1) mixture, heated to reflux until the solid completely dissolved. Removing heating, the resulting solution was naturally cooled to 20 to 25° C. under stirring, producing precipitates. The obtained solid was filtered and dried to afford a crystalline form (1.60 g, yield: about 80%).

The XRPD spectrum, the DSC graph and the TGA graph of the obtained crystalline form were substantially the same as those in Example 1, indicating crystalline form A was obtained.

Example 3

The compound of Formula (I) (2 g) was added to 12 mL N,N-dimethylformamide, stirred until the solid completely dissolved. Then, 48 mL purified water was added dropwise thereto at room temperature under stirring, producing precipitates. The obtained solid was filtered and dried to afford a crystalline form (1.60 g, yield: about 80%).

The XRPD spectrum, the DSC graph and the TGA graph of the obtained crystalline form were substantially the same as those in Example 1, indicating crystalline form A was obtained.

Example 4

The compound of Formula (I) (5 g) was added to 60 mL acetonitrile and dissolved by heating, and oxalic acid (1.4 g) was added under reflux to precipitate a solid. The precipitates were filtered, and 50 mL purified water was added to the obtained filter cake. The pH was adjusted to 9-10 with aqueous ammonia, and a crystalline form was precipitated by stirring at 0° C. to 25° C. The precipitates were filtered and dried to afford crystalline form B (4.5 g, yield: about 90%).

The obtained crystalline form B was subjected to XRPD analysis, and the resulting XRPD spectrum is shown in FIG. 4, comprising peaks at diffraction angles (2θ) of about 6.4±0.2, 7.9±0.2, 8.4±0.2, 11.8±0.2, 12.7±0.2, 15.5±0.2, 16.0±0.2, 16.3±0.2, 16.9±0.2, 19.1±0.2 and 23.5±0.2 degrees.

The obtained crystalline form B was subjected to DSC analysis, and the resulting graph is shown in FIG. 5. According to this analysis, the obtained crystalline form B had endothermic peaks at (77.5±0.5)-(84.7±0.5)° C., (87.0±0.5)-(97.3±0.5)° C. and (192.1±0.5)-(195.3±0.5)° C.

The obtained crystalline form B was subjected to TGA analysis, and the resulting graph is shown in FIG. 6. According to this analysis, the obtained crystalline form B has three characteristic peaks, and the peak positions are at about 82.0±0.5° C., 271.0±0.5° C. and 331.0±0.5° C., respectively.

Experimental Example 1

Viscous Fluidity Test

A measuring container was filled with crystalline form B (1.97 g) of the compound of Formula (I), and the volume was determined to be 7.62 ml without applying any external force. The most apparent density (i.e., bulk density) was calculated to be 0.26 g/ml. The powder was slowly added into a funnel from above so that the material leaking from the bottom of the funnel formed a conical stack on the horizontal surface, and the diameter of the bottom of the cone (2R) and the height of the cone (H) were measured to be 3.59 cm and 1.79 cm, respectively. And the angle of repose was calculated to be 45 degrees according to the formula for calculating the angle of repose (tan α=H/R).

A measuring container was filled with crystalline form A (4.18 g) of the compound of Formula (I), and the volume was determined to be 9.78 ml without applying any external force. The most apparent density (i.e., bulk density) was calculated to be 0.43 g/ml. The powder was slowly added into a funnel from above so that the material leaking from the bottom of the funnel formed a conical stack on the horizontal surface, and the diameter of the bottom of the cone (2R) and the height of the cone were measured to be 2.91 cm and 1.46 cm, respectively. And the angle of repose was calculated to be 45 degrees according to the formula for calculating the angle of repose (tan α=H/R).

The above experiments show that both crystalline form A and crystalline form B of the compound of Formula (I) of the present invention have good particle fluidity, which are convenient for mixing directly and uniformly with other adjuvants during preparation of a formulation, and are beneficial to the improvement of the accuracy of the content of the active pharmaceutical ingredients. Specifically, crystalline form A and crystalline form B of the compound of Formula (I) of the present invention have good fluidity during the preparation of capsules, tablets, and granules, and the particles have a smooth surface and do not agglomerate, which facilitates patients' consumption.

Experimental Example 2

Physicochemical Stability

Crystalline form A and crystalline form B (about 0.1 g, respectively) of the compound of Formula (I) prepared in the examples of the present invention were placed under high temperature (60° C.), high humidity (92.5%) or light condition, respectively, for 5 days, and the crystalline forms were subjected to XRPD and HPLC analysis before and after the placement, respectively, to determine changes in crystalline form and purity. The experimental results are shown in the table below.

| Crystalline form | Initial HPLC purity (area %) | Placement condition | Changes in crystalline form | Relative purity after placement |
|---|---|---|---|---|
| Crystalline form A of the compound of Formula (I) | 99.8% | Placed under high temperature (60° C.) for 5 days | No | 100% |
| Crystalline form A of the compound of Formula (I) | 99.8% | Placed under high humidity (92.5%) for 5 days | No | 100% |
| Crystalline form A of the compound of Formula (I) | 99.8% | Placed under light condition for 5 days | No | 100% |
| Crystalline form B of the compound of Formula (I) | 99.5% | Placed under high temperature (60° C.) for 5 days | No | 100.04% |
| Crystalline form B of the compound of Formula (I) | 99.5% | Placed under high humidity (92.5%) for 5 days | No | 100% |
| Crystalline form B of the compound of Formula (I) | 99.5% | Placed under light condition for 5 days | No | 100% |

* "Relative purity" refers to the ratio of HPLC purity after placement to the initial HPLC purity.

From the above results, it can be seen that crystalline forms A and B of the compound of Formula (I) of the present invention have almost no change in purity under high temperature, high humidity or light condition, and no crystalline form changes occur before and after the placement, which indicates that not only crystalline forms A and B of the compound of Formula (I) of the present invention are stable under high humidity condition, high temperature condition or light condition, but also their stabilities are not affected by air (especially oxygen) under such conditions. Thus they have very excellent physicochemical stabilities. In particular, crystalline form A of the compound of Formula (I) of the present invention not only can be directly prepared in high purity according to the method of the present application, but also has very excellent stability under high temperature, high humidity and/or light condition. The above experimental results indicate that the crystalline forms of the compound of Formula (I) of the present invention have no special requirements on the transportation conditions, and do not require special conditions such as sealing, exclusion of light, low temperature, etc., and can ensure the quality and safety of the product even after transportation and storage under high humidity, high temperature and/or light condition (it can be ensured that no impurities generating when the crystalline forms of the compound of Formula (I) of the present invention are placed under high temperature and/or high humidity conditions for a long time), thereby ensuring the safety of the clinical medication.

Experimental Example 3 hERG Test

The effects of the crystalline forms of the compound of Formula (I) on hERG potassium channel were determined using a biochemical hERG assay kit based on fluorescence polarization technology (Predictor™ hERG Fluorescence Polarization Assay Kit, Thermo Fisher) to assess the potential of the crystalline form of the compound of Formula (I) in inducing cardiac QT interval prolongation. The crystalline form of the compound of Formula (I) (test concentration: 3, 10 and 30 μM) was added to a microwell plate containing hERG cell membrane, followed by a tracer with high hERG affinity After incubating the microwell plate at 25° C. for 2 h, change of fluorescence polarization value was detected using BMG PHAREStar multimode reader, and percent inhibition (%) at different concentrations was calculated, and the range of half maximal inhibitory concentration ($IC_{50}$) of the crystalline form of the compound of Formula (I) was obtained. The experimental results are shown in Table 1.

TABLE 1

| hERG test results | |
|---|---|
| Crystalline form | $IC_{50}$ (μM) |
| Crystalline form A | >30 |

The test indicates that crystalline form A of the compound of Formula (I) of the present invention has a hERG inhibition rate of less than 50% at a concentration of 30 μM, and crystalline form A of the compound of the present invention has an $IC_{50}$ of more than 30 μM, which indicates that crystalline form A of the compound of the present invention has no hERG-related toxicity, and will not cause toxic and side effects of QT interval prolongation as a clinical medication.

Experimental Example 4

Cytotoxicity

The cells were plated at a concentration of $2\times10^4$ cells/well and incubated for 4 h at 37° C. in a 5% $CO_2$ incubator. The crystalline form of the compound of Formula (I) of the present invention was added, and incubation was continued for 40 h. The incubation solution was removed, and a complete medium was added (100 μl/well) to each test well and incubated in the incubator for 0.5 to 1 h. Then, MTS solution was added (10 μl/well) thereto, and incubation was continued for 4 h in the incubator. The absorbance at 450 nm was measured, and the $IC_{50}$ value was calculated. The results are shown in Table 2.

TABLE 2

Cytotoxicity test results

| Crystalline form | IC$_{50}$ (μM) | | |
|---|---|---|---|
| | HEK293 | HK-2 | N2a |
| Crystalline form A | >50 | 23.13 | 33.56 |

Note:
HEK293 is a human embryonic kidney cell; HK-2 is a human proximal tubular cell; and N2a is a neuroblastoma cell.

The results show that crystalline form A of the compound of Formula (I) of the present invention has low cytotoxicity to different kinds of cells of human body, and particularly has almost no cytotoxicity to human embryonic kidney cells, which indicates that crystalline form A of the compound of Formula (I) of the present invention is very safe as a clinical medication, and especially can be used safely in patients with kidney disease.

Experimental Example 5

JAK1, JAK2, JAK3 and TYK2 Enzymatic Activity Inhibition Assay

The crystalline form of the compound of Formula (I), an enzyme, a substrate and ATP were diluted to desired concentrations with the buffer in the HTRF® KinEASE™-TK kit (Cisbio). The former three agents were added into a multiple well plate, and incubated at room temperature after being mixed homogeneously. ATP was added to initiate the kinase reaction, and incubation at room temperature was performed. The test reagent in the kit was used to terminate the reaction, and incubation was continued at room temperature. After the incubation was completed, fluorescence signals at 620 nm and 665 nm were measured using a BMG PHERAstar FS microplate reader, and the half inhibitory concentration (IC$_{50}$) values were calculated. The results are shown in Table 3.

TABLE 3

Inhibition of JAK activity

| Crystalline form | JAK1 (IC$_{50}$, nM) | JAK2 (IC$_{50}$, nM) | JAK3 (IC$_{50}$, nM) | TYK2 (IC$_{50}$, nM) |
|---|---|---|---|---|
| Crystalline form A | 1.28 ± 0.17 | 0.65 ± 0.06 | 16.10 ± 1.55 | 22.80 ± 4.03 |

The data in Table 3 show that crystalline form A of the compound of Formula (I) shows potent inhibition of JAK1 and JAK2 kinase activity, and has certain selectivity compared to inhibition of JAK3 and TYK2, the same family of JAK1 and JAK2 kinases, indicating that crystalline form A of the compound of Formula (I) of the present invention has great pharmacodynamic potential against the targets JAK1 and JAK2.

Experimental Example 6

Effect on JAK/STAT Signaling Pathway in Hep3B Cells

After incubating the crystalline form of the compound of Formula (I) of the present invention with Hep3B cells in a 37° C., 5% CO$_2$ incubator for 15 min, 40 ng/μL IL-6 was added. Incubation was continued for 30 min, and the cells were lysed. The lysate was added to AlphaLISA SureFire Ultra p-STAT3 (Tyr705) assay kit (PerkinElmer), incubated at room temperature in dark, and the signals emitted by the receptor microbeads after energy absorption were measured, and the half inhibitory concentration (IC$_{50}$) of inhibiting STAT3 phosphorylation was calculated. The results are shown in Table 4.

TABLE 4

Inhibitory activity of the compound on STAT3 phosphorylation

| Crystalline form | p-STAT3 (IC$_{50}$, nM) |
|---|---|
| Crystalline form A | 123.15 ± 18.32 |

The data in Table 4 indicate that crystalline form A of the compound of Formula (I) of the present invention has a good inhibitory activity against phosphorylation of STAT3, a downstream kinase of the JAK/STAT signal in Hep3B cells.

Experimental Example 7

Efficacy in Collagen-Induced Arthritis (CIA) Model in Rats

After female Lewis rats were immunized twice with bovine type II collagen to form a CIA model, the rats were randomly divided into 4 groups (the vehicle group, and the groups of the crystalline form of the compound of Formula (I) of the present invention (1 mg/kg, 3 mg/kg, 10 mg/kg), respectively), and unmodeled rats were taken as the normal group. The corresponding drugs were administered by gavage once a day for 14 days (D15-D28). The hind paw was scored for arthritis index during the administration (the results are shown in Table 5); and after the end of the experiment, the ankle joint was taken for pathologic analysis (the average pathological scores of the hind paw joints of the rats are shown in Table 6).

TABLE 5

Hind paw arthritis index scores of CIA model rats during administration (X̄ ± SD)

| Group/test days | D15 | D17 | D20 | D24 | D28 |
|---|---|---|---|---|---|
| 1/vehicle group | 7.60 ± 0.70 | 7.90 ± 0.32 | 7.90 ± 0.32 | 8.00 ± 0.00 | 8.00 ± 0.00 |
| 2/crystalline form A 1 mg/kg | 7.50 ± 1.08 | 7.50 ± 1.08 | 7.70 ± 0.48 | 7.50 ± 0.53 | 7.10 ± 0.88 |
| 3/crystalline form A 3 mg/kg | 7.50 ± 0.85 | 6.60 ± 0.97 | 5.70 ± 1.34 | 4.90 ± 1.37 | 4.50 ± 1.43 |
| 4/crystalline form A 10 mg/kg | 7.50 ± 0.85 | 4.90 ± 0.57 | 2.80 ± 0.92 | 2.30 ± 0.67 | 1.30 ± 0.67 |

The results of the hind paw arthritis index scores show that crystalline form A of the compound of Formula (I) of the present invention can relieve the swelling of the hind paw joint of the CIA model rats and reduce the arthritis index score of the animals in a dose-dependent manner. 3 mg/kg, 10 mg/kg of crystalline form A of the compound of Formula (I) of the present invention can significantly reduce the hind paw arthritis index scores during D17-D28. 1 mg/kg of crystalline form A of the compound of Formula (I) of the present invention reduces the arthritis index score to some extent. At 10 mg/kg arthritis index scores were decreased to the greatest extent.

TABLE 6

Mean pathological scores of hind paw joints in CIA modeled rats ($\bar{X} \pm SD$)

| Group/parameter | Joint inflammation | Joint cartilage erosion | Synovial hyperplasia/ pannus |
|---|---|---|---|
| 1/vehicle group | 5.60 ± 0.52 | 7.70 ± 0.48 | 8.00 ± 0.00 |
| 2/crystalline form A 1 mg/kg | 4.00 ± 1.25 | 5.10 ± 1.52 | 6.90 ± 0.99 |
| 3/crystalline form A 3 mg/kg | 2.60 ± 1.90 | 2.20 ± 1.93 | 4.80 ± 1.40 |
| 4/crystalline form A 10 mg/kg | 0.30 ± 0.67 | 0.10 ± 0.32 | 2.20 ± 0.42 |

The results of the pathological scores of the hind paw joints show that crystalline form A of the compound of Formula (I) of the present invention can relieve the hind paw joint lesion of the CIA model rats and reduce the mean pathological scores in a dose-dependent manner. 3 mg/kg, 10 mg/kg of crystalline form A of the compound of Formula (I) of the present invention can significantly reduce the mean pathological scores of joint inflammation, joint cartilage erosion and synovial hyperplasia/pannus. 1 mg/kg of crystalline form A of the compound of Formula (I) of the present invention can significantly reduce the mean pathological scores of joint inflammation and joint cartilage erosion, and reduce the mean pathological score of synovial hyperplasia/pannus to some extent.

In summary, in the CIA modeled Lewis rats, the crystalline form of the compound of Formula (I) of the present invention can reduce the arthritis index scores and reduce the mean pathological scores (the mean pathological scores of joint inflammation, joint cartilage erosion, synovial hyperplasia/pannus) in a dose-dependent manner. The crystalline form of the compound of Formula (I) of the present invention can be effective at a low dose (e.g., 1 mg/kg), and 10 mg/kg of crystalline form of the compound of Formula (I) of the present invention has the best improvement effect.

The above specific embodiments further describe the present invention in details. However, the scope of the above-mentioned subject matter of the present invention should not be construed as being limited to the above examples, and the technical solutions implemented based on the disclosure of the present invention are all within the scope of the present invention.

What is claimed is:
1. A crystalline form of the compound of Formula (I), which is crystalline form A of the compound of Formula (I):

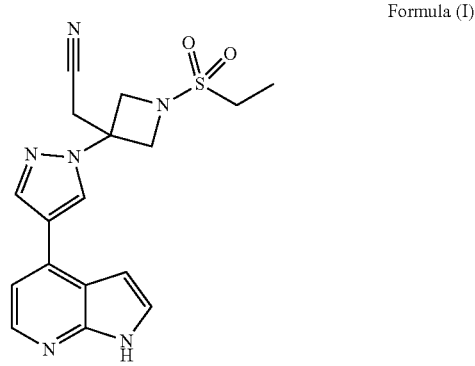 [SMILES: CCS(=O)(=O)N1CC(CC#N)(n2cc(-c3ccnc4[nH]ccc34)cn2)C1]

Formula (I)

the XRPD spectrum of the crystalline form A comprises peaks at diffraction angles (2θ) of about 10.2±0.2, 11.5±0.2, 13.5±0.2, 14.6±0.2, 17.8±0.2, 18.5±0.2, 18.7±0.2, 19.9±0.2 degrees.

2. The crystalline form A of the compound of Formula (I) of claim 1, the XRPD spectrum thereof comprises peaks at diffraction angles (2θ) shown in FIG. 1, and the XRPD peak positions are shown in FIG. 1.

3. The crystalline form A of the compound of Formula (I) of claim 2, the DSC graph of the crystalline form A comprises a characteristic peak at about (190.6±0.5)-(194.5±0.5)° C.

4. The crystalline form A of the compound of Formula (I) of claim 3, the TGA graph of the crystalline form A comprises two characteristic peaks at about 272.7±0.5° C. and 347.2±0.5° C.

5. A method for the preparation of the crystalline form A of the compound of Formula (I) of claim 1, comprising adding the compound of Formula (I) to a solvent, heating and stirring to dissolve it, then removing heating, and allowing the resulting solution to be cooled under stirring, and filtering the solid precipitate from the solution to afford the crystalline form A.

6. A method for the preparation of the crystalline form A of the compound of Formula (I) of claim 2, comprising adding the compound of Formula (I) to a solvent, heating and stirring to dissolve it, then removing heating, and allowing the resulting solution to be cooled under stirring, and filtering the solid precipitate from the solution to afford the crystalline form A.

7. A method for the preparation of the crystalline form A of the compound of Formula (I) of claim 1, comprising dissolving the compound of Formula (I) in a solvent to the formed solution, stirring to allow formation of a solid precipitate, and filtering the precipitated solid to afford the crystalline form A.

8. A method for the preparation of the crystalline form A of the compound of Formula (I) of claim 2, comprising dissolving the compound of Formula (I) in a solvent to the formed solution, stirring to allow formation of a solid precipitate, and filtering the precipitated solid to afford the crystalline form A.

9. The method of claim 5, wherein the weight/volume ratio (g/mL) of the compound of Formula (I) to the solvent is 1:1 to 1:80.

10. The method of claim 6, wherein the weight/volume ratio (g/mL) of the compound of Formula (I) to the solvent is 1:1 to 1:80.

11. The method of claim 5, wherein the solvent is a mixed solvent of two solvents, the volume ratio between the two solvents is (1-30):(30-1).

12. The method of claim 6, wherein the solvent is a mixed solvent of two solvents, the volume ratio between the two solvents is (1-30):(30-1).

13. The method of claim 5, wherein the temperature at the end of the cooling is 10-30° C.

14. The method of claim 6, wherein the temperature at the end of the cooling is 10-30° C.

15. The method of claim 7, wherein the volume ratio of the solvent to the antisolvent is (0.2-1):(1-20).

16. The method of claim 8, wherein the volume ratio of the solvent to the antisolvent is (0.2-1):(1-20).

17. The method of claim 7, wherein the weight/volume ratio (g/mL) of the compound of Formula (I) to the solvent is 1:(1-20).

18. The method of claim 8, wherein the weight/volume ratio (g/mL) of the compound of Formula (I) to the solvent is 1:(1-20).

19. A crystalline form of the compound of Formula (I), which is crystalline form B of the compound of Formula (I):

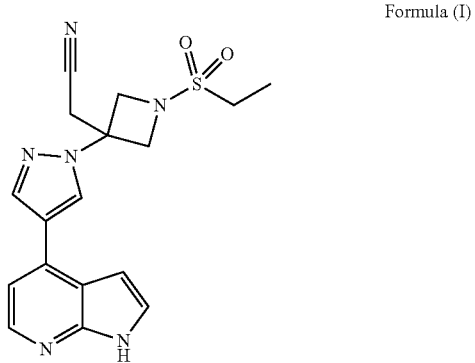 [SMILES: CCS(=O)(=O)N1CC(CC#N)(n2cc(-c3ccnc4[nH]ccc34)cn2)C1]

Formula (I)

the XRPD spectrum of the crystalline form B comprises peaks at diffraction angles (2θ) of about 6.4±0.2, 7.9±0.2, 8.4±0.2, 11.8±0.2, 12.7±0.2, 15.5±0.2, 16.0±0.2, 16.3±0.2, 16.9±0.2, 19.1±0.2 degrees.

20. The crystalline form B of the compound of Formula (I) of claim 19, the XRPD spectrum thereof comprises peaks at diffraction angles (2θ) shown in FIG. 4, and the XRPD peak positions are shown in FIG. 4.

21. A method for the preparation of the crystalline form B of the compound of Formula (I) of claim 19, comprising reacting the compound of Formula (I) with an acid in an organic solvent, filtering the precipitated salt, adding it to an inorganic solvent to react with a base, or a hydroxide, an acetate, a carbonate or bicarbonate of an alkali metal or an alkaline earth metal, and filtering the precipitated solid to afford the crystalline form B.

22. A method for the preparation of the crystalline form B of the compound of Formula (I) of claim 20, comprising reacting the compound of Formula (I) with an acid in an organic solvent, filtering the precipitated salt, adding it to an inorganic solvent to react with a base, or a hydroxide, an acetate, a carbonate or bicarbonate of an alkali metal or an alkaline earth metal, and filtering the precipitated solid to afford the crystalline form B.

23. A pharmaceutical composition comprising the crystalline form A of the compound of Formula (I) of claim 1 and one or more pharmaceutically acceptable carriers.

24. A pharmaceutical composition comprising the crystalline form A of the compound of Formula (I) of claim 2 and one or more pharmaceutically acceptable carriers.

25. A pharmaceutical composition comprising the crystalline form B of the compound of Formula (I) of claim 19 and one or more pharmaceutically acceptable carriers.

26. A pharmaceutical composition comprising the crystalline form B of the compound of Formula (I) of claim 20 and one or more pharmaceutically acceptable carriers.

27. A method for the reversing, alleviating, or inhibiting the progress of a JAK-related disease, comprising administering to a subject in need thereof an effective amount of the crystalline form A of the compound of Formula (I) of claim 1, wherein the JAK-related diseases are selected from the group consisting of rheumatoid arthritis, atopic dermatitis, psoriasis, myeloproliferative disorders, chronic myeloid leukemia, head and neck cancer, prostate cancer, pancreatic cancer, multiple myeloma, neuroblastoma, and kidney disease.

28. A method for the reversing, alleviating, or inhibiting the progress of a JAK-related disease, comprising administering to a subject in need thereof an effective amount of the crystalline form A of the compound of Formula (I) of claim 2, wherein the JAK-related diseases are selected from the group consisting of rheumatoid arthritis, atopic dermatitis, psoriasis, myeloproliferative disorders, chronic myeloid leukemia, head and neck cancer, prostate cancer, pancreatic cancer, multiple myeloma, neuroblastoma, and kidney disease.

29. A method for the reversing, alleviating, or inhibiting the progress of a JAK-related disease, comprising administering to a subject in need thereof an effective amount of the pharmaceutical composition according to claim 23, wherein the JAK-related diseases are selected from the group consisting of rheumatoid arthritis, atopic dermatitis, psoriasis, myeloproliferative disorders, chronic myeloid leukemia, head and neck cancer, prostate cancer, pancreatic cancer, multiple myeloma, neuroblastoma, and kidney disease.

30. A method for the reversing, alleviating, or inhibiting the progress of a JAK-related disease, comprising administering to a subject in need thereof an effective amount of the pharmaceutical composition according to claim 24, wherein the JAK-related diseases are selected from the group consisting of rheumatoid arthritis, atopic dermatitis, psoriasis, myeloproliferative disorders, chronic myeloid leukemia, head and neck cancer, prostate cancer, pancreatic cancer, multiple myeloma, neuroblastoma, and kidney disease.

31. The crystalline form A of the compound of Formula (I) of claim 1, the XRPD spectrum comprises peaks at diffraction angles (2θ) of about 10.2±0.2, 11.5±0.2, 13.5±0.2, 14.6±0.2, 17.8±0.2, 18.5±0.2, 18.7±0.2, 19.9±0.2, 20.5±0.2, 23.0±0.2 and 26.8±0.2 degrees.

32. The crystalline form A of the compound of Formula (I) of claim 2, the DSC graph of the crystalline form A comprises a characteristic peak at a temperature shown in FIG. 2, and the characteristic peak position in the DSC graph of crystalline form A is shown in FIG. 2.

33. The crystalline form A of the compound of Formula (I) of claim 3, the TGA graph of the crystalline form A comprises characteristic peaks at a temperature shown in FIG. 3, and the characteristic peak positions in the TGA graph of crystalline form A are shown in FIG. 3.

34. A method for the preparation of the crystalline form A of the compound of Formula (I) of claim 1, comprising adding the compound of Formula (I) to an alcohol solvent, a nitrile solvent, a ketone solvent, an ether solvent, a halogenated alkane solvent, an amide solvent, an ester solvent, or a mixed solvent formed by two or more of the above solvents, heating and stirring to dissolve it, then removing heating, and allowing the resulting solution to be cooled under stirring, and filtering the solid precipitate from the solution to afford the crystalline form A.

35. A method for the preparation of the crystalline form A of the compound of Formula (I) of claim 2, comprising adding the compound of Formula (I) to an alcohol solvent, a nitrile solvent, a ketone solvent, an ether solvent, a halogenated alkane solvent, an amide solvent, an ester solvent, or a mixed solvent formed by two or more of the above solvents, heating and stirring to dissolve it, then removing heating, and allowing the resulting solution to be cooled under stirring, and filtering the solid precipitate from the solution to afford the crystalline form A.

36. A method for the preparation of the crystalline form A of the compound of Formula (I) of claim 1, comprising dissolving the compound of Formula (I) in an alcohol solvent, a nitrile solvent, a ketone solvent, an ether solvent, a halogenated alkane solvent, an amide solvent, an ester solvent, then adding water to the formed solution, stirring to allow formation of a solid precipitate, and filtering the precipitated solid to afford the crystalline form A.

37. A method for the preparation of the crystalline form A of the compound of Formula (I) of claim 2, comprising dissolving the compound of Formula (I) in an alcohol solvent, a nitrile solvent, a ketone solvent, an ether solvent, a halogenated alkane solvent, an amide solvent, an ester solvent, then adding water to the formed solution, stirring to allow formation of a solid precipitate, and filtering the precipitated solid to afford the crystalline form A.

38. The method of claim 5, wherein the weight/volume ratio (g/mL) of the compound of Formula (I) to the solvent is 1:5 to 1:30.

39. The method of claim 5, wherein the weight/volume ratio (g/mL) of the compound of Formula (I) to the solvent is 1:10, 1:15, 1:20, 1:25, 1:40, 1:50, 1:60, or 1:70.

40. The method of claim 6, wherein the weight/volume ratio (g/mL) of the compound of Formula (I) to the solvent is 1:5 to 1:30.

41. The method of claim 6, wherein the weight/volume ratio (g/mL) of the compound of Formula (I) to the solvent is 1:10, 1:15, 1:20, 1:25, 1:40, 1:50, 1:60, or 1:70.

42. The method of claim 5, wherein the solvent is a mixed solvent of two solvents, the volume ratio between the two solvents is 1:5, 1:10, 1:15, 1:20, 1:25, 1:30, 30:1, 25:1, 20:1, 15:1, 10:1, 5:1, or 1:1.

43. The method of claim 6, wherein the solvent is a mixed solvent of two solvents, the volume ratio between the two solvents is 1:5, 1:10, 1:15, 1:20, 1:25, 1:30, 30:1, 25:1, 20:1, 15:1, 10:1, 5:1, or 1:1.

44. The method of claim 5, wherein the temperature at the end of the cooling is 20-25° C.

45. The method of claim 6, wherein the temperature at the end of the cooling is 20-25° C.

46. The method of claim 7, wherein the volume ratio of the solvent to the antisolvent is 1:(1-10).

47. The method of claim 8, wherein the volume ratio of the solvent to the antisolvent is 1:(1-10).

48. The method of claim 7, wherein the weight/volume ratio (g/mL) of the compound of Formula (I) to the solvent is 1:(1-10).

49. The method of claim 8, wherein the weight/volume ratio (g/mL) of the compound of Formula (I) to the solvent is 1:(1-10).

* * * * *